United States Patent [19]

Poland et al.

[11] Patent Number: 5,128,244
[45] Date of Patent: Jul. 7, 1992

[54] ASSAY FOR DIOXINS

[75] Inventors: Alan P. Poland; Christopher A. Bradfield, both of Madison; Edward N. Glover, Mt. Horeb, all of Wis.; Andrew S. Kende, Pittsford; Frank H. Ebetino, Norwich, both of N.Y.

[73] Assignee: Wisconsin Alumni Research Foundation, Madison, Wis.

[21] Appl. No.: 300,725

[22] Filed: Jan. 25, 1989

Related U.S. Application Data

[63] Continuation of Ser. No. 50,189, May 14, 1987, abandoned.

[51] Int. Cl.$^5$ .................................. G01N 33/53
[52] U.S. Cl. ........................ 435/7.8; 435/7.93; 435/975; 436/501; 436/503; 436/504; 436/545; 436/804; 436/808; 436/822; 549/339
[58] Field of Search ............ 436/501, 503, 504, 545, 436/804, 808, 822; 549/339; 435/7.1, 7.8, 7.93, 975

[56] References Cited

U.S. PATENT DOCUMENTS 4,238,472 12/1980 Albro et al. .................. 436/825
4,544,629 10/1985 Rice et al. .................. 436/503

OTHER PUBLICATIONS

Denison et al., *Eur. J. Biochem.* 147:2, 429-435 (1985).
P. Albro et al., 50 Tox. Appl. Pharm. 137-146 (1979).
F. Ebetino, Design of a Probe for the TCDD Receptor, University of Rochester, Part II of Doctoral Thesis, pp. 71-124 (pp. i-vii) (1984).
A. Poland et al., 251 J. Biol. Chem. 4936-4946 (1976).
A. Poland et al., 261 J. Biol. Chem. 6352-6365 (May 15, 1986).
J. Denny et al., 81 P.N.A.S. USA 5286-5290 (1984).
J. Cadogan et al., J. Chem. Soc. (Perkins 1) 541-42 (1973).

*Primary Examiner*—Esther L. Kepplinger
*Assistant Examiner*—Carol A. Spiegel
*Attorney, Agent, or Firm*—Quarles & Brady

[57] ABSTRACT

A screening assay for recognizing the presence of dioxins (and other related toxins) in a sample is disclosed. In one aspect of the invention, Ah receptor from mice and a radioactively labelled halogenated dioxin are used in a competitive binding assay to test for the presence of toxins. The label is $^{125}$I substituted directly on the main dioxin structure. The relative binding of the toxin in the samples (in competition with labelled dioxin) for Ah receptor can be compared against standard curves. A kit is provided for running such an assay and a preferred $^{125}$I ligand is provided.

11 Claims, 1 Drawing Sheet

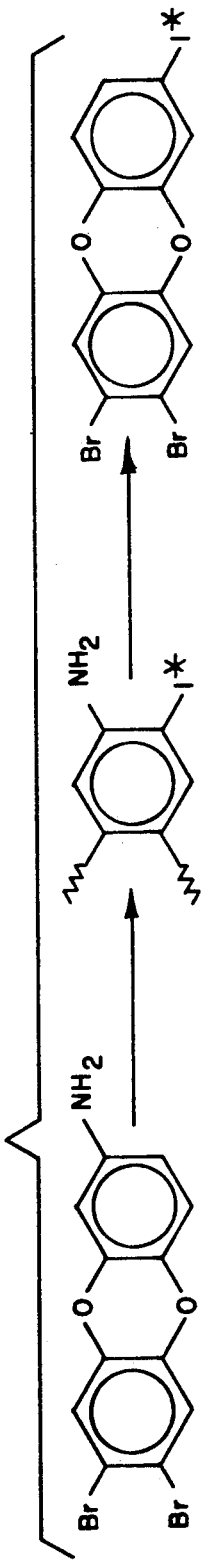
| | R₁ | R₂ | R₃ | R₄ | R₆ | R₇ | R₈ | R₉ |
|---|---|---|---|---|---|---|---|---|
| TCDD | H | Cl | Cl | H | H | Cl | Cl | H |
| PENTACHLORO | Cl | Cl | Cl | H | H | Cl | Cl | H |
| HEXACHLORO | Cl | Cl | Cl | H | H | Br | Cl | Cl |
| TRI-BDD | H | Br | Br | H | H | Br | H | H |
| TBDD | H | Br | Br | H | H | Br | Br | H |
| DI-BROMO | H | Br | Br | H | H | H | H | H |
| TCDD-CN | CN | Cl | Cl | H | H | Cl | Cl | H |
FIG. 2
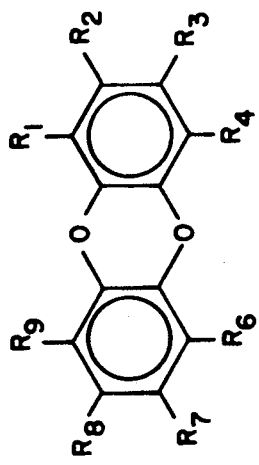
FIG. 1
FIG. 3
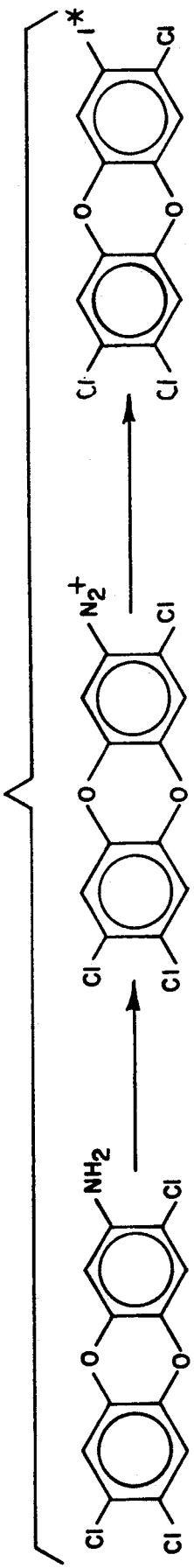
FIG. 4

ASSAY FOR DIOXINS

This invention was made with United States government support awarded by the Department of Health & Human Services (NIH), Grant number(s): R01ES01884, P30CA07175, and T32CA09020. The United States Government has certain rights in this invention.

This application is a continuation of application Ser. No. 07/50,189 filed May 14, 1987, now abandoned.

The present invention relates to assays for aromatic halogenated toxins such as those in the dioxin family, and to compounds and kits useful in connection with such assays. More particularly it relates to the use of radioactive halogenated dioxin compounds in competitive binding assays.

BACKGROUND OF THE INVENTION 2,3,7,8-tetrachloro-dibenzo-p-dioxin ("TCDD") is one of the most potent small molecule toxins known to man. It was a contaminant in the Vietnam defoliant known as "Agent Orange". The widespread dispersion of dioxins such as TCDD in our environment, their resistance to degradation, their lipophilicity (and hence accumulation in the food chain), and their toxic potency have all led to concern about the hazards they pose. Considerable effort has therefore been devoted to monitoring the concentration of these compounds.

Testing for trace concentrations of these compounds in environmental and biological samples has been made possible through recent advances in chromatographic and mass spectral technologies. These methods usually involve varying degrees of sample preparation, separation of isomers by liquid or gas chromatography, and identification and quantification of related compounds by mass spectrometry. Despite the sensitivity of mass spectrometer methods, their use is limited by cost and the availability of instrumentation.

Bioassays, such as the formation of pericardial edema in newborn chicks or production of chloracne in rabbit ears, played a prominent early role in the identification and monitoring of chlorinated dibenzo-p-dioxins. Bioassays using cell cultures (e.g., induction of aryl hydrocarbon hydroxylase activity in rat hepatoma cells o keratinization in XB/3T3 cells, have achieved appreciable sensitivity (approximately 10 pg), but have not gained widespread use. The primary reasons such methods are not widely used are that they are time consuming, costly, and suffer from the variability inherent in using whole cells.

Radioimmunoassays (using antibodies and certain radioactively labelled ligands) to detect dioxins have been developed with sensitivities of approximately 25 pg. See generally P. Albro et al., 50 Tox. Appl. Pharm. 137-146 (1979). The limited use of such RIA techniques to date with dioxins may be attributed to 1) the need to characterize each antisera for its reactivity towards a large number of isomers and interfering compounds; 2) difficulties in the solubility of antigen; and 3) lack of and/or cost of optimal radioligands. In this regard, dioxins are too small to efficiently form antibodies until they are altered with complex linking structures.

It has also been known that dioxins exert their biological effects via stereospecific binding to a soluble protein, the aryl hydrocarbon hydroxylase receptor ("Ah receptor"). Attempts have therefore been made to competitively bind Ah receptor to $C^{14}$ and $^3H$ radioactive variants of dioxins as an assay technique. However, such compounds have proven to have unacceptably low specific activity for commercial assays or other problems. Radioactive ligands having appropriate activity and appropriate stability, specificity, and solubility, vis a vis Ah receptor have not to date been developed. Thus, it can be seen that the need exists for an improved assay for dioxins.

SUMMARY OF THE INVENTION

In one aspect, there is provided an assay for the presence in a sample of a halogenated dibenzo-p-dioxin. One competitively exposes Ah receptor to the halogenated dibenzo-p-dioxin in the sample and also to a radioactively labelled halogenated dibenzo-p-dioxin. In accordance with the invention, at least one radioactive halogen, preferably $^{125}I$, is the radioactive label. One then compares the resulting radioactivity against a known control. One can separate the Ah bound radioactive dioxin from the unbound radioactive dioxin and then test the radioactivity of either the bound fraction or the unbound fraction (depending upon how a standard curve is set up). Preferably, at least two of the $R_2$, $R_3$, $R_7$, and $R_8$ positions on the dioxin structure are halogen (at least one of which is radioactive), and postions R7 and R8 are halogen.

In another aspect of the invention there is provided a competitive assay kit. It has Ah receptor and a radioactively labelled halogenated dibenzo-p-dioxin. Radioactive halogen is the radioactive label.

In another aspect of the invention, $[^{125}I]$-2 iodo-7,8 dibromo-dibenzo-p-dioxin is provided.

An object of the invention therefore includes providing an assay of the above kind in which halogenated dioxins can be assayed for.

Another object is to provide an assay of the above kind which is simple, relatively inexpensive, and easy to perform.

Another object is to provide kits and radioactively labelled compounds useful in an assay of the above kind. Still other objects and advantages of the present invention will be apparent from the description which follows.

DESCRIPTION OF THE DRAWINGS

A better understanding of the present invention will be accomplished by reference to the drawings. It should be understood, however, that the drawings and the description of the preferred embodiments are merely examples of the invention. They are not intended to represent the full scope of the invention. Rather, the claims should be looked to in order to determine the full scope of the invention.

FIG. 1 depicts the basic chemical structure of halogenated dibenzo-p-dioxins, with the letters $R_1$, R, $R_3$, $R_4$, $R_6$, $R_7$, $R_8$, and $R_9$ indicating substitution positions on the basic framework;

FIG. 2 is a chart describing some of the more common halogenated dioxins;

FIG. 3 is a schematic synthesis of the preferred radio labelled dioxin; and

FIG. 4 is a schematic syntheses of a second preferred radio labelled dioxin.

DESCRIPTION OF THE PREFERRED EMBODIMENTS

Materials

Active Charcoal, grade PX-21 was purchased from Amoco Research Corp., Chicago, Ill.; Bacto-Gelatin from Difco Laboratories, Detroit, Mich.; Magnesium sulfate from Fisher Scientific Co., Fair Lawn, N.J.; Ammonium sulfate (ultrapure) from Schwarz/Mann, Cambridge, Mass.; Methanol (HPLC grade) from Burdick and Jackson Laboratories Inc., Muskegan, Mich.; Glycerol from J. T. Baker, Phillipsburg, N.J.; EDTA from EM Scientific, Cherry Hill, N.J.; Carrier free $NA^{125}I$ (NE2-033L) was from New England Nuclear, North Billerica, Mass.; Dithiothreitol, Beta-mercaptoethanol, sodium azide, chloramine-T, and MOPS (free acid and sodium salt) were purchased from Sigma Chemical Co., St. Louis, MO; Dichloromethane (reagent grade), tetrahydrofuran (anhydrous, 99.9% pure), n-butyl nitrite (97% pure), p-dioxane (anhydrous 99+% pure), and dimethyl sulfoxide (anhydrous, 99% pure, stored under $N_2$ gas) were purchased from Aldrich Chemical Co., Milwaukee, Wis.

The buffer "MDENG" contained 25 mM MOPS, 1mM dithiothreitol, 1 mM EDTA, 0.02% sodium azide, and 10% glycerol, pH 7.5 (at 4° C). "MSSENG" represents the above buffer with Betamercaptoethanol (10 mM) substituted for dithiothreitol. "MEN" represents the above buffers without the addition of thiol reducing agents, or glycerol. "MN" buffer contained 25 mM MOPS, 0.02% sodium azide, pH 7.5 (at 4° ).

Ah Receptor Preparation

The Ah receptor is described in A. Poland et al., 251 J. Biol. Chem. 4936–4946 (1976). The disclosure of this article and all other articles recited herein are incorporated herein by reference as if fully set forth herein. Ah receptor can be obtained from mice as follows:

C57BL/6J mice were purchased from The Jackson Laboratory, Bar Harbor, Me., and bred in our laboratory. See generally A. Poland et al., 261 J. Biol. Chem. 6352-65 (May 15, 1986) (not prior art). One-hundred adult male and female mice were killed by cervical dislocation, their livers removed, rinsed with ice cold KCl (150 mM), homogenized in 9 vol of MSSENG buffer, and centrifuged at 10,000 xg for 20 min at 4° C. The post-mitochondrial supernatant was carefully removed to avoid contamination by the surface lipid layer, and subjected to centrifugation at 105,000 x g. The supernatant (approx. 10 mg protein/ml) was separated from surface lipids and the microsomal pellet, and stored at −80° C. until processed further.

The frozen cytosolic fraction was thawed, and placed in an ice bath with slow stirring. A saturated solution of ammonium sulfate in MEN buffer was added to the cytosolic preparation, to a final concentration of 40%, over a period of 30 min, and stirred for an additional 30 min. The solution was centrifuged at 10,000 x g for 20 min, the supernatant fraction removed, slowly brought to an ammonium sulfate concentration of 55%, stirred for an additional 30 min, centrifuged at 10,000xg, and the supernatant discarded. The 40–55% ammonium sulfate precipitate was resuspended in 55% ammonium sulfate in MN, and aliquots equivalent to 0.5 g wet weight of liver (15 mg protein) were placed in 12×75 mm borosilicate tubes (VWR Scientific, San Francisco, Calif.), and spun at 5000xg. The supernatant was removed by careful aspiration, and the pellets were stored in stoppered tubes at −80° C. until use.

Synthesis Of [$^{125}$I]-2-iodo-7,8-dibromo-dibenzo-p-dioxin

This synthesis was performed in a room dedicated to radiosynthesis, equipped with a high flow chemical hood, with the use of sealed vials and airtight syringes to minimize escape of radioiodine. The entire procedure was monitored with a gamma radiation detector. The synthesis is depicted in FIG. 3.

To 5 mCi of carrier free $Na^{125}I$ ($\geq$350 mCi/ml in 6 mM NaOH, $\leq$15 ul of water) in a septum-sealed conical vial was added 2.5 nmol of 2-amino-7,8-dibromodibenzo-p-dioxin (See A. Poland et al. 261 J. Biol. Chem. 6352, 6354 (1986) (not prior art);25 ul of methanol, 1.13 umol of sulfuric acid in 10 ul of methanol/water (9:1), and 25 nmol of chloramine-T in 5 ul methanol. See J. Denny et al., 81 P.N.A.S. USA 5286-5290 (1984) for somewhat analogous procedures.

The iodination reaction was complete in 30 minutes and terminated by the addition of 500 ug of sodium metabisulfite and 5 umol sodium hydroxide in 35 ul water. The reaction product, [$^{125}$I]-2-amino-3-iodo-7,8-dibromodibenzo-p-dioxin, was extracted with 250 ul of dichloromethane with the use of a vortex mixer (30 sec.). The organic phase was aspirated into a syringe (gas syringe, pressure-locked plunger tip, P010032, Pierce Chemical Co., Rockford, Ill.) transferred to a 1 ml sealed conical vial (Reacti-vial 13221, Pierce Chemical Co.) containing 10 mg of magnesium sulfate, 75 ul of dichloromethane and a microstirring bar, and the mixture stirred for 45 min to dry the organic phase.

The NH2 group was removed by generation of the aryldiazonium salt ($N_2^+$, which produces the aryl radical with subsequent abstraction of hydrogen from tetrahydrofuran to form the deaminated product. See generally J. Cadogan et al., J. Chem. Soc. (Perkins 1) 541–42 (1973) for somewhat analogous procedures. To do this, the dried dichloromethane solution was aspirated and transferred to a 1 ml conical vial containing 250 ul anhydrous tetrahydrofuran and 67 umol n-butyl nitrite. The reaction mix was then heated at 55° C. with stirring.

After 15 minutes, the vial was opened, and the solvent evaporated, with heating, under a stream of nitrogen gas, venting the vial into a funnel (2 cm dia.) attached to two serially-connected charcoal filters in line with negative airflow. This system trapped most of the volatile radioiodine in the first charcoal filter, and minimized release into the laboratory hood ventilation system. The reaction mix solute was dissolved in 50 ul of methanol:water (92:8) and the [$^{125}$I]-labelled product purified by high performance liquid chromatography as detailed below.

Assay Protocol

To a series of 12×75 borosilicate assay tubes was added 5 ul of DMSO containing TCDD standards (0,5,10,20,40,60,100, 200,500, and 1000 fmoles) or unknowns. The 40-55% ammonium sulfate Ah precipitate (15 mg protein in a frozen aliquot) was dissolved in ice cold MDENG buffer and diluted to a conc. of 150 ug protein/ml (equivalent to an Ah receptor conc. of 18-20 fmol/ml). The radioligand in DMSO was added to the solution of receptor to a conc. of fmole/ul (40,000 dpm/ul, added as 1 ul stock solution/ml buffer) and incubated for 5 min at 4° C., before adding 1 ml of the solution to each assay tube. The tubes were stored at 4° C. in a refrigerator for 16 hours.

The assay was terminated by the addition of a 0.5 ml of suspension of charcoal/gelatin (3%/0.3%) in MN buffer with vigorous stirring on a vortex mixer for 3 sec., and incubated for 10 min at 4° C. Dioxin bound to Ah stayed in solution, whereas unbound dioxin bound to the charcoal/gel atin. The tubes were centrifuged at 2000 xg for 10 min at 4° C. A one ml aliquot of the supernatant fraction of each tube was transferred to 12×75 ml polypropylene tubes (VWR Scientific, San Francisco, CA), and the Ah bound radioligand quantified in a MINAXI Series-5000 gamma scintillation counter (United Technologies/Packard Instrument Co., Downer Grove, Ill.).

Approximately 10% of the radioligand added adsorbs to the silica test tube walls, and this adsorption is increased by vortexing. We recommend vortexing only in the termination of the assay. The results were compared against standard curves. Statistical analysis of the standard curve of the specifically bound radioligand v. the log of the concentration of competing TCDD, indicated the minimal detectable concentration of TCDD to be 10 pM (3.2 pg in a 1 ml assay). By a reduction in the total assay volume to 0.25 ml, the minimal detectable amount of TCDD was reduced to 0.8 pg. A radioligand concentration of 7.2 pM (35,000 dpm/ml) and a receptor concentration of 18-20 pM (150 ug protein/ml) was found to yield the best sensitivity.

[$^{125}$I]decays to tellurium with a half-life of 60 days. Thus, radiodecay could produce unlabelled 2,3-dibromodibenzo-p-dioxin in the radioligand stock solution. We tested whether radioligand decay products might compete for receptor binding and diminish radioligand binding. Assays run using the stock solution of radioligand 120 days after its synthesis showed no significant deviation in the quality control parameters when compared to freshly prepared radioligand. Thus, surprisingly, repurification of the radioligand by HPLC does not appear necessary for at least 120 days after synthesis.

Environmental Assay

This competitive binding assay can also be used to screen environmental samples for the presence of compounds which compete for the Ah receptor. Such compounds in the environment include polycyclic aromatic hydrocarbons, halogenated armomatic hydrocarbon, chlorinated-dibenzo-p-dioxin, dibenzofuran, azoxybenzene and biphenyl isomers, and brominated biphenyls. If desired, polycyclic aromatic carbons can be eliminated from analysis prior to assay by appropriate conventional sample cleanup. The method of sample cleanup preparation will, of course, depend on the nature of the sample (e.g., biological tissue, soil, water, etc.) and the presence of interfering substances. After positive results on screening, samples could be further analyzed by the more costly mass spectrum methods.

One example of a clean-up technique is:

Place 50 g diced cow liver tissue in 100 ml $H_2SO_4$ (conc.) for 16 hr. Partition the solution against 100 ml hexane in a separatory funnel three times (keeping the 300 ml of hexane). Extract the 300 ml against (50 ml×3) of fresh $H_2SO_4$ to further purify. Filter the hexane through $M_gSO_4$ to dry the hexane fraction. Remove the hexane via a rotatory evaporator, leaving a residue. Dissolve the residue in 500 microliters of hexane. Take one half of the volume and load it onto 2 g of silica.

Elute with hexane, collecting the third through fifth ml. Evaporate the 3 ml under $N_2$. Redissolve the residue in 200 ml of ethanol. Inject 100 microliters onto HPLC. The 17th portion is collected, dried under N2, and redissolved in 100 ml DMSO for use in the assay.

Synthesis Of
$^{125}$I-2-iodo-3,7,8-trichlorodibenzo-p-dioxin

FIG. 4 depicts the synthesis.

To 50 ug of 2-amino-3,7,8-trichlorodibenzo-p-dioxin, A. Poland et al., 261 J. Biol. Chem. 6352-6365 (1986), was added 30 ul of ice-cold 50% $H_2SO_4$. After stirring the solution for 10 minutes at 0° C., 6 ul of $NaNO_2$ (10 ug/ul) was added. This solution was then stirred for 30 minutes at 0° C., followed by the addition of 2 ul urea (100 ug/ul) to destroy excess nitrous acid. This solution was stirred for 2 minutes at 0° C., whereupon one half its volume (approximately 19 ul) was added to an ice cold solution of Na$^{125}$I (5mCi, 218Ci/mmol) in 20 ul of 6 mM NaOH. Following a 2 hour incubation at 20° C., the iodination reaction was terminated by the addition of 200 ul of 1.35N NaOH, 0.1M Na (pH 8.0), and 2 mg/ml $Na_2S_2O_5$. The crude [$^{125}$I]-2-iodo3,7,8-trichlorodibenzo-p-dioxin was then extracted into 200 ul of CHC13 and subjected to HPLC purification (retention time 24 minutes).

While specific radioactive ligands have been discussed above, the invention is not so limited. Compounds having at least two halogens at R, $R_3$, $R_7$, and $R_8$ are highly preferred as are compounds with H at $R_1$, $R_4$, $R_6$, and $R_9$, as are compounds with $^{125}$I substituted at the R, $R_3$, $R_7$, and/or $R_8$ positions.

It is also expected that certain substitutions other than H or Halogen (e.g. $CH_3$) at the R positions may prove useful ligands for such assays. Further, Ah receptor from other animals besides just mice may have acceptable utility.

We claim:

1. A method of assaying a sample for the presence of a halogenated dibenzo-p-dioxin of formula (1)

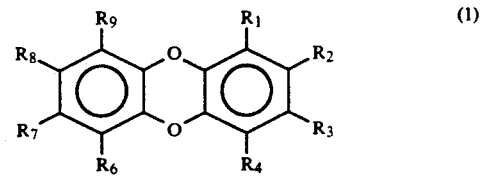

wherein
$R_1$, $R_3$, $R_7$, $R_8$ and $R_9$ are each independently hydrogen or halogen,
$R_2$ is halogen, and
$R_4$ and $R_6$ are hydrogen,
comprising:
contacting said sample with an aryl hydrocarbon hydroxylase receptor (Ah) and a competitor consisting essentially of a radioactive iodine labelled derivative of the formula (1) halogenated dibenzo-p-dioxin, wherein at least one of $R_2$ or $R_3$ is radioactive iodine, until equilibrium binding occurs;
separating Ah bound labelled competitor from unbound labelled competitor;
measuring the radioactivity of either the bound or free labelled competitor; and
comparing the measured radioactivity to a standard curve as an indication of the presence of said halogenated dibenzo-p-dioxin in said sample.

2. The method of claim 1, wherein the radioactive iodine is $^{125}I$.

3. The method of claim 1, wherein the competitor has the following substitutions in formula (1):

$R_1 = H$,
$R_2 = {}^{125}I$,
$R_3 =$ halogen or H,
$R_4 = H$,
$R_6 = H$,
$R_7 =$ halogen or H,
$R_8 =$ halogen or H,
$R_9 = H$, and at least two of $R_2$, $R_3$, $R_7$ and $R_8$ are halogen.

4. The method of claim 3, wherein the competitor has the following substitutions in formula (1):

$R_1 = H$,
$R_2 = {}^{125}I$,
$R_3 = H$,
$R_4 = H$,
$R_6 = H$,
$R_7 = Br$,
$R_8 = Br$, and
$R_9 = H$.

5. A kit for assaying a sample for the presence of a halogenated dibenzo-p-dioxin of formula (1)

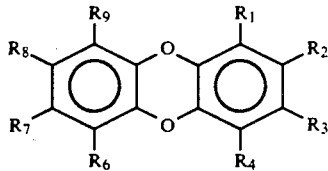

wherein $R_1$, $R_3$, $R_7$, $R_8$ and $R_9$ are each independently hydrogen or halogen, $R_2$ is halogen, and $R_4$ and $R_6$ are hydrogen, comprising, in one or more containers:

an aryl hydrocarbon hydroxylase receptor (Ah); and a competitor consisting essentially of a radioactive iodine labelled derivative of the formula (1) halogenated dibenzo-p-dioxin, wherein at least one of $R_2$ or $R_3$ is radioactive iodine.

6. The kit of claim 5, wherein the radioactive iodine is $^{125}I$.

7. The kit of claim 6, wherein the competitor has the following substitutions in formula (1):

$R_1 = H$,
$R_2 = {}^{125}I$,
$R_3 =$ halogen or H,
$R_4 = H$,
$R_6 = H$,
$R_7 =$ halogen or H,
$R_8 =$ halogen or H,
$R_9 = H$, and at least two of $R_2$, $R_3$, $R_7$ and $R_8$ are halogen.

8. The kit of claim 7, wherein the competitor has the following substitutions in formula (1):

$R_1 = H$,
$R_2 = {}^{125}I$,
$R_3 = H$,
$R_4 = H$,
$R_6 = H$,
$R_7 = Br$,
$R_8 = Br$, and
$R_9 = H$.

9. A 3-[$^{125}I$]iodo-7, 8-dibromo-dibenzo-p-dioxin competitor synthesized by a method comprising $^{125}I$ iodinating a 7, 8-dibromo-dibenzo-p-dioxin that has the formula (1) of claim 5 except that it has a nitrogen containing moiety at the $R_2$ substitution so as to provide $^{125}I$ at the $R_3$ substitution, followed by replacing the nitrogen containing moiety with a hydrogen.

10. The competitor of claim 9, wherein the nitrogen containing moiety is an amino group.

11. The competitor of claim 10, wherein the hydrogen replacement of the amino group after iodination comprises generation of an aryl diazonium salt intermediate.

* * * * *